(12) United States Patent
Frant

(10) Patent No.: US 12,048,436 B2
(45) Date of Patent: Jul. 30, 2024

(54) FILLING MATERIAL FOR TREATING CHRONIC VENOUS INSUFFICIENCY AND A CORRESPONDING INSERTION METHOD

(71) Applicant: Miikka Frant, Oulu (FI)

(72) Inventor: Miikka Frant, Oulu (FI)

( * ) Notice: Subject to any disclaimer, the term of this patent is extended or adjusted under 35 U.S.C. 154(b) by 182 days.

(21) Appl. No.: 17/415,622

(22) PCT Filed: Dec. 13, 2019

(86) PCT No.: PCT/FI2019/050891
§ 371 (c)(1),
(2) Date: Jun. 17, 2021

(87) PCT Pub. No.: WO2020/128154
PCT Pub. Date: Jun. 25, 2020

(65) Prior Publication Data
US 2022/0054142 A1 Feb. 24, 2022

(30) Foreign Application Priority Data
Dec. 18, 2018 (FI) ...................................... 20186105

(51) Int. Cl.
*A61B 17/12* (2006.01)
*A61B 17/00* (2006.01)

(52) U.S. Cl.
CPC .. *A61B 17/12131* (2013.01); *A61B 17/12031* (2013.01); *A61B 17/12109* (2013.01);
(Continued)

(58) Field of Classification Search
CPC ........ A61B 17/12131; A61B 17/12031; A61B 17/12109; A61B 17/12177;
(Continued)

(56) References Cited

U.S. PATENT DOCUMENTS

| 5,002,556 A | * | 3/1991 | Ishida | ............... A61B 17/12136 |
| | | | | 604/103.1 |
| 2005/0107867 A1 | | 5/2005 | Taheri | |

(Continued)

FOREIGN PATENT DOCUMENTS

| EP | 2471462 A1 | 7/2012 |
| WO | 99/13779 A2 | 3/1999 |

(Continued)

OTHER PUBLICATIONS

International Search Report and Written Opinion, issued by the International Searching Authority (ISA/EP) in PCT Application No. PCT/FI2019/050891 dated Apr. 3, 2020. 11 pages.

(Continued)

*Primary Examiner* — Sarah A Long
*Assistant Examiner* — Raihan R Khandker
(74) *Attorney, Agent, or Firm* — Meunier Carlin & Curfman LLC

(57) ABSTRACT

The present invention introduces a material, i.e. a device, which is insertable into a vein of a outer parts of a sheath, two-sidedly adhesive tubular material with a supporting material and protrusions, either a balong or an inner protective film, and a control cable for the insertion and extraction of the device along the vein. The supporting material may be compressed initially, and after removal of the outer part of the sheath, the supporting material with protrusions will expand towards the vein walls. After removal of the inner part of the sheath and the control cable, the treated vein area can be manually pressed on top of the skin, thus closing the vein through inner and outer adherence of the material. The protrusions may have a barbed shape.

22 Claims, 4 Drawing Sheets

(52) U.S. Cl.
CPC .............. *A61B 17/12177* (2013.01); *A61B 2017/00398* (2013.01); *A61B 2017/00557* (2013.01); *A61B 2017/00862* (2013.01); *A61B 2017/00942* (2013.01); *A61B 2017/00951* (2013.01); *A61B 2017/12081* (2013.01)

(58) Field of Classification Search
CPC ........... A61B 2017/12081; A61B 2017/00557; A61B 2017/00942; A61B 2017/00951
See application file for complete search history.

(56) References Cited

U.S. PATENT DOCUMENTS

| | | | | |
|---|---|---|---|---|
| 2006/0009798 | A1* | 1/2006 | Callister | A61B 17/12181 623/1.22 |
| 2006/0074478 | A1* | 4/2006 | Feller, III | A61B 17/12118 623/1.11 |
| 2007/0248640 | A1* | 10/2007 | Karabey | A61B 17/0057 424/423 |
| 2013/0184658 | A1 | 7/2013 | Duncan | |
| 2015/0018857 | A1 | 1/2015 | Elgaard et al. | |
| 2015/0265283 | A1* | 9/2015 | Leanna | A61B 17/068 606/41 |
| 2021/0219980 | A1* | 7/2021 | Truosolo | A61B 17/12022 |

FOREIGN PATENT DOCUMENTS

| | | |
|---|---|---|
| WO | 2010/022072 A2 | 2/2010 |
| WO | 2015/187196 A1 | 12/2015 |

OTHER PUBLICATIONS

Finnish Patent and Registration Office. Search Report issued in U.S. Appl. No. 20/186,105 dated Aug. 30, 2019. 2 pages.

Vici Venous Stent (R) System—P180013. Overview of Information related to FDA approval to market of product. Downloaded on Jun. 9, 2021 from https://www.fda.gov/medical-devices/recently-approved-devices/vici-venous-stentr-system-p180013. 2 pages.

Covidien. Parietex ProGrip (TM) Self-Fixating Mesh. Value Analysis Committee Product Information Kit. 2010. 17 pages.

\* cited by examiner

FILLING MATERIAL FOR TREATING CHRONIC VENOUS INSUFFICIENCY AND A CORRESPONDING INSERTION METHOD

PRIORITY

This is a U.S. national stage application of international application number PCT/FI2019/050891 filed on Dec. 13, 2019, which claims priority to FI20186105 filed on Dec. 18, 2018, the contents of both of which are incorporated herein by reference.

FIELD OF THE INVENTION

The present invention relates to medical appliances in surgical operations, especially in treating chronic venous insufficiency (CVI).

BACKGROUND OF THE INVENTION

Chronic venous insufficiency (CVI) is a medical condition where blood pools in veins and thus, strains the walls of the vein. CVI occurs especially in the legs, and it can be seen as the lack of capability in the returning blood flow from the extremities of the body back to the heart. CVI can also be considered to result from a certain lack of functioning venous valves (i.e. reflux of the venous valves), resulting in the fact that the blood will pool in the veins. The signs and symptoms of the CVI comprise varicose veins, itching, increased pigmentation in the affected area, chronic swelling and ulcers.

Traditionally, CVI or varicose veins have been treated with performing a local anesthetic surgery. Milder treatment methods are conservative methods, and they include compression stockings, and guiding the patient to sleep in a position where the feet locate above the heart. In surgeries, ligation has been used, i.e. the tying off a vein for preventing the blood flow. The vein can be operated through venous exhavesion, which means the same as vein stripping, i.e. pulling out the vein using minimal number of incisions. There are methods for inserting energy towards the surrounding tissue within the vein, which destroys the interior of the vein wall, i.e. the intima of the vein. The destruction of an intima of the desired vein results in clogging the path of the flowing blood, which is the desired effect with these methods. Endovenous laser ablation (i.e. endovenous laser treatment/ELT) is one of these energy transferring methods, meaning that optical fiber is inserted into the vein and usually infrared laser light is directed onto the interior of the vein, which leads into formation of scar tissue. The result is a clogged vein. The laser light can be replaced with using RF ("Radio Frequency") energy. The RF signal will burn the interior of the vein, thus closing the blood flow in the vein. Pulses of steam can be directed to the interior of the vein. Even foam can be inserted into the vein for preventing the blood flow through it, and the foam can be used to create an artificial inflammation in the vein. A drawback of the use of foam is that it will not work for veins having a diameter over 6 mm. Another drawback of the foam is that it may create irritation within the body based on its chemical properties, and the fact that it is not natural substance within the human body. The drawbacks of the laser and RF signal based methods are that many injections are required for creating tuminence around the vein before the actual energy transfer towards the intima of the vein. Furthermore, the use of laser or RF energy results in creating internal excessive heat well above the regular body temperature of the patient, meaning that even the surrounding healthy tissues may suffer from burns resulting from conducted thermal energy. There are also risk of complications which include bruising, hematoma, temporary numbness, phlebitis, induration and a sensation of tightness after the operation. As more serious complications, they include skin burns, deep venous thrombosis, pulmonary embolism and nerve injury. Also the accidental use of a laser light outside of the patient's body may represent danger to the eye. One drawback in using laser based technology and also RF based technology is the high cost required when purchasing a laser light source equipment or a RF signal source (i.e. an RF transmitter with appropriate antenna).

Also some metal structures have been used especially in arteries. The used materials in such applications have been steel, cobolt, chrome or nitinol (nickel titanium). With such metal structures, the purpose is usually to keep an artery open.

One drawback in metal structures is that the substance will remain in the patient's body after the operation and thus, it may have secondary or later effects in the surrounding tissue.

One drawback in current treating methods of the CVI is that many methods contain the risk of creating nerve damages in the leg of the patient. For instance, the thigh and the lower leg comprise the great saphenous vein (lat. "vena saphena magna") and the small saphenous vein (lat. "vena saphena parva"), respectively. Heat generating methods applying laser or RF signal may lead to damage (i.e. burns) in the surrounding healthy tissue around the small saphenous vein of the lower leg, and this at its worst, can lead to nerve damage in the affected area of the lower leg. This can result to insensibility of the heel of the patient, which will not cure over time. This is a major and life-quality weakening problem for the patient in the currently used methods involving heat or intrusion into the surrounding healthy tissues e.g. through surgical intervention.

Among actual products in the market, "Vici Venous Stent" by Boston Scientific Corporation is a tubular stent applicable in the vein. Its structure is a compressable tube-like form, where there is a cell type of structure along the twistable tube. The cell shape is a bit reformulated rectangular shape slightly misaligned on top of one another along the surface. The whole structure is formed by thin wires forming the cell structure. The stent is made of nitinol.

The prior art comprises a product called "ProGrip" from Medtronic Ltd (initially from Covidien plc before the merger), as disclosed in "Parietex ProGrip™ Self-Fixating Mesh", Value Analysis Committee, Product Information Kit. ProGrip may be used in inguinal and ventral hernia repairs, comprising incisional hernia repairs. Also laparoscopic inguinal hernia repairs may be performed using ProGrip self-fixating mesh product. The main characteristic of ProGrip mesh is the shape of its protrusions, which includes "dual bubbles" in the end of each protrusion. Such a shape will penetrate the tissue surface during hernia surgeries and the shape ensures that the mat or the mesh with such a protrusion shape will remain connected in the tissue even when forces apply in the mesh area. The material of ProGrip is "Bicomponent mesh constructed of hydrophilic monofilament polyester (PET) knit with resorbable polylactic acid (PLA) microgrips". This hydrophilic material will self-fixate totally and does not require any sutures.

The problem is ProGrip based products is that they are used currently in hernia repair surgeries only, and the structure has been optimised in view of that application area only.

SUMMARY OF THE INVENTION

The present invention introduces a new way of treating the chronic venous insufficiency (CVI). The method and the device can be used in situations where efficient closure of the vein is desired without the drawbacks present in the currently used prior art methods and devices. In the core of the invention is a new type of material, which is insertable into a vein of the patient, the material being shaped in a tubular form. Such material has adhering properties in both the inner and outer surfaces of the material. In the following, the material is disclosed as a device which comprises several layers with different functionalities, and which device is in principle a tubularly shaped structure insertable into the vein of the patient. The device does not require electricity but it is a manually operable element which has removable and transformable parts as disclosed in the detailed description.

In other words, the present invention introduces a device applicable to insertion into a vein of a human patient. The present invention is characterized in that the device is a tubular device and it comprises:
 a control cable made of metal, which is insertable into the vein,
 a sheath with an inner and outer part, the inner part of the sheath having a central tunnel for the control cable, where the inner and the outer parts of the sheath are able to slide in relation to one another and in relation to the control cable into the vein and inside the vein,
 two-sidedly adhesive tubular material between the inner and outer parts of the sheath, where
 the diameter of the two-sidedly adhesive tubular material is expandable either in self-acting fashion or as a response to pressure originating from inserted liquid inside the tubular material after the outer part of the sheath has been removed, when the outer adhesive surface of the tubular material is capable to attach to an intima of the vein, where further
 the adhesive properties for the tubular material are created by protrusions extending from both surfaces of the tubular material, and after the removal of the inner part of the sheath and the control cable,
 through manual pressing force applied to the skin of the patient along the area of the treated vein, the inner adhesive surface of the tubular material is capable to attach with its own counter-surface, thus closing the vein within two-sidedly adhered area of the tubular material.

In an embodiment of the invention, the outer part of the sheath is a protective film with hydrofilic properties, which protective film is manually removable from the vein or towards outside of the vein through a pulling movement.

In an embodiment of the invention, the protrusions are shaped as thorns, spines, prickles, arrows, or as blunt or sharply shaped barbs, or as curved hooks, either with or without a drop-shaped thicker end part.

In an embodiment of the invention, the protrusions comprise plurality of branches and sub-branches, where each of the ends of the sub-branches are shaped as barbs or hooks.

In an embodiment of the invention, the two-sidedly adhesive tubular material comprises a compressable network structure or otherwise elastic material which is able to self-expand or to expand under applied force when the outer part of the sheath is pulled outwards from the device and the vein.

In an embodiment of the invention, the device comprises a balong inside the tubular material, which balong is fillable at least partly with a liquid, creating a force expanding the tubular material in an outwards direction towards the inner surface of the vein.

In an embodiment of the invention, the device comprises an inner protective film without a balong, configured to prevent the adhesive inner surface of the tubular structure to stick to itself before the expansion of the diameter of the tubular material in the vein has taken place.

In an embodiment of the invention, the outer part of the sheath is configured to have a hydrofilic surface or coating allowing slidable motion of the sheath inside the vein.

In an embodiment of the invention, the inner part and the outer part of the sheath are slidable longitudinally in relation to one another which movement releases the adhesive surface to expand either in self-expanding fashion, or through the filling of the balong with a liquid.

In an embodiment of the invention, the device comprises non-dissolving material protrusions in given longitudinal locations of the tubular material allowing the device to fix and maintain within the inner surface of the vein over time.

In an embodiment of the invention, the device comprises dissolving material protrusions longitudinally between the non-dissolving material protrusions, which dissolving material protrusions will keep initially attached to the inner surface of the vein after removal of the device, and thereafter, the dissolving material protrusions are configured to dissolve by white blood cells of the human body over time.

In an embodiment of the invention, the device comprises non-dissolving material protrusions symmetrically along at least two longitudinally directed lines along the surface of the tubular material, while the rest of the protrusions are made of dissolving material.

In an embodiment of the invention, the dissolving material is processed collagen or monocryl, and the non-dissolving material comprises metal.

In an embodiment of the invention, the two-sidedly adhesive tubular material comprises a supporting material, which supporting material is at least partly manufactured from dissolving material.

In an embodiment of the invention, the length L of the protrusions is selected between the range of 0.5 mm L 1.0 mm, thus allowing the protrusions to penetrate the intima of the vein into the muscle layer.

In an embodiment of the invention, a section in an insertable end of the control cable into the human vein is curvable and thinner cable in view of the rest of the control cable, allowing smooth progress of the control cable with a manual rotating movement along the insertion process.

In an embodiment of the invention, the device is configured to be removable partly from the vein after its insertion, where first the outer part of the sheath is manually pulled out partly from the vein, thereafter the two-sidedly adhesive tubular material is diametrically expanded either in self-acting fashion or through a manually fillable balong, thereafter the inner part of the sheath without a balong or with an emptied balong is configured to be manually removable from the treated area of the vein, whereafter the control cable is manually pullable out from the treated area of the vein, resulting in only the adhesive tubular material comprising a supporting material and the protrusions to remain in the treated area of the vein before the manual pressing action is performed to the treated area of the vein.

In an embodiment of the invention, the treatment of the vein is configured to be performed in a step-wise manner for a given longitudinal length at a time while a part of the outer part of the sheath remains in the surgical cut of the vein to prevent blood loss during the treatment.

In an embodiment of the invention, the outer part of the sheath is splittable into two longitudinal halves when outside the vein during a pulling movement or slidable longitudinally on top of the inner part of the sheath, and the inner part of the sheath is slidable along the control cable with a pulling movement, the inner and the outer parts of the sheath also slidable in relation to one another.

In an embodiment of the invention, an outer surface of the inner part of the sheath comprises a visible measurement scale assisting in treated sub-length selection.

In an embodiment of the invention, the device comprises alternating sections of the two-sidedly adhesive tubular material and mere supporting material, where the mere supporting material comprises non-dissolving material acting as a sealing plug for the migrating metallic protrusions.

In an embodiment of the invention, the two-sidedly adhesive tubular material is manufactured from two adjacent and opposite layers with protrusions which layers are sewn or otherwise connected together.

In an embodiment of the invention, the protrusions are aligned in at least two different directions when inspecting an opened, planar adherable material within its single surface.

In an embodiment of the invention, a proper force applied towards the intima of the vein is configured to be verified by a pressure measurement of the liquid insertion means of the balong.

In an embodiment of the invention, the end result of the process of closing the vein is configured to be verified by an ultrasound measurement performed for each treated sub-length of the vein after or during that particular sub-length has been or is manually pressed.

DETAILED DESCRIPTION OF THE INVENTION

The present invention introduces a device which is insertable manually into a vein of a patient suffering e.g. from CVI. The device is a longitudinal, tubular structure with various different functional parts, in layer-like arrangement.

The purpose of the invention is to provide a device which is easily insertable to a vein of the patient after a surgical cut is performed to a desired location of the patient's body, usually in the great saphenous vein (lat. vena saphena magna), or in the small saphenous vein (lat. vena saphena parva). The great saphenous vein runs along the whole leg, while small saphenous vein runs in the lower leg area between popliteal vein (lat. vena poplitea) and dorsal venous arch of the foot. The area to be treated can locate between the ankle and the knee in the lower leg area or between the knee and the groin in the thigh area, or both. The treated area may even locate near the knee of the patient in either the lower leg side or the thigh side depending where the treated vein is located. This is possible because the inserted material is designed to be thin and basically elastic material, and at least partially made of dissolvable material(s). Furthermore, the treatment can be applied to the Giacomini vein which locates in the thigh area between the great and small saphenous veins. Furthermore, an anterolateral branch of the great saphenous vein can be treated as well with the inventive concept.

At first, a puncture is made to the skin to access the vein to be treated, i.e. a venipuncture is performed by a surgeon, a doctor or a specialist called a phlebotomist. When the vein access is gained, a thin control cable may be inserted into the punctured hole in the skin. The control cable may have a special characteristic where its end part forms a thinner, curvable part in view of the rest of the control cable. This means when the entered control cable is pushed by the medical specialist into the vein, and along the vein, the cable will face the interior walls of the vein often because the shape of the vein is usually very curvy. When the thin end of the cable faces an interior "wall" of the vein because a curve in the vein shape, by rotating the control cable manually and simultaneously entering the cable, the end of the cable will find the free direction along the vein "tunnel". As the next curve is faced along the vein, the medical specialist can again rotate the control cable so that the thin end angle will turn into the free direction along the interior of the vein. This way, the control cable may be fed along the vein to the location which is to be treated in the following steps.

Figure 1:
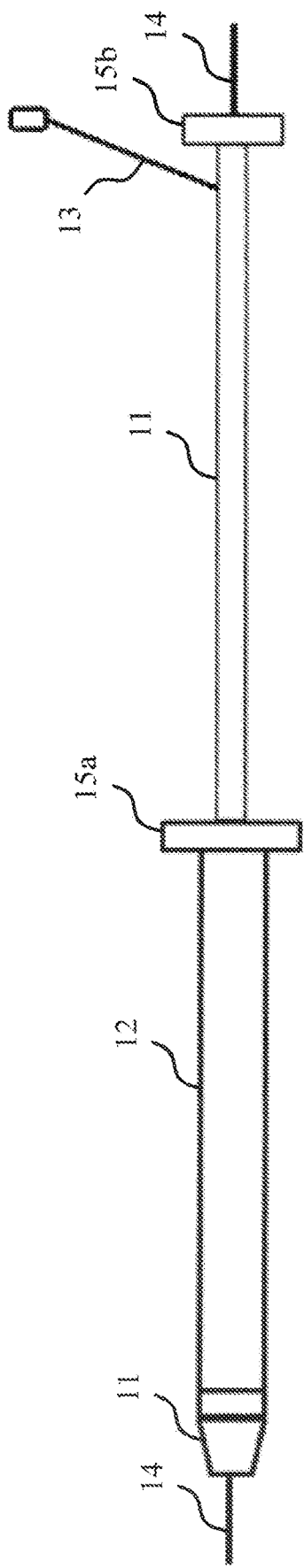
FIG. 1 illustrates the outer structure of the device in a schematic fashion in an example of the invention.

Next we refer to FIG. 1, where the control cable 14 is shown as a horizontal wire in both the left hand side and right hand side of the device in FIG. 1. The possible thin end of the control cable 14 locates then in the left hand side of the depicted control cable 14. The other parts of the device comprise a sheath where the outer part 12 of the sheath and the inner part 11 of the sheath are slidable in relation to one another. The inner part 11 of the sheath is also visible as the blunt left hand side end of the device. The holding means 15a, 15b can be grabbed and pulled together in order to perform one or more process steps, such as removing a protective film within the sheath structure (discussed later in more detail). With the pulling movement to the holding means 15a-b, the inner part of the sheath 11 slides within the outer part of the sheath 12 in longitudinal direction. The control cable 14 is freely movable in a central tunnel of the sheath, or to be more precise, the sheath is longitudinally movable along the control cable 14 when the sheath is entered into and along the human vein after the control cable 14 has been inserted. The present invention may apply a balong, which as a separate entity is known from prior art, but in connection to the presented application area of vein treatment, the balong as part of the invented device has been an unintroduced element. The input path and filling route for the balong is shown as 13, comprising a small liquid reservoir and conduit for the liquid used for filling the balong. The details of the balong structure and operational principle are discussed later. The balong can be used in principle in a similar fashion as a balloon catheter in a percutaneous coronary intervention but the application area is totally different in this case of vein treatment, and also the end result is different between these two application areas. In coronary interventions the balong is used to achieve an open path for the blood flow, while in the present invention the balong is used as part of a process which ends in a closure of the vein, i.e. stopping the blood flow in that particular vein, through usage of a two-sidedly adherable tubular material.

Figure 2:
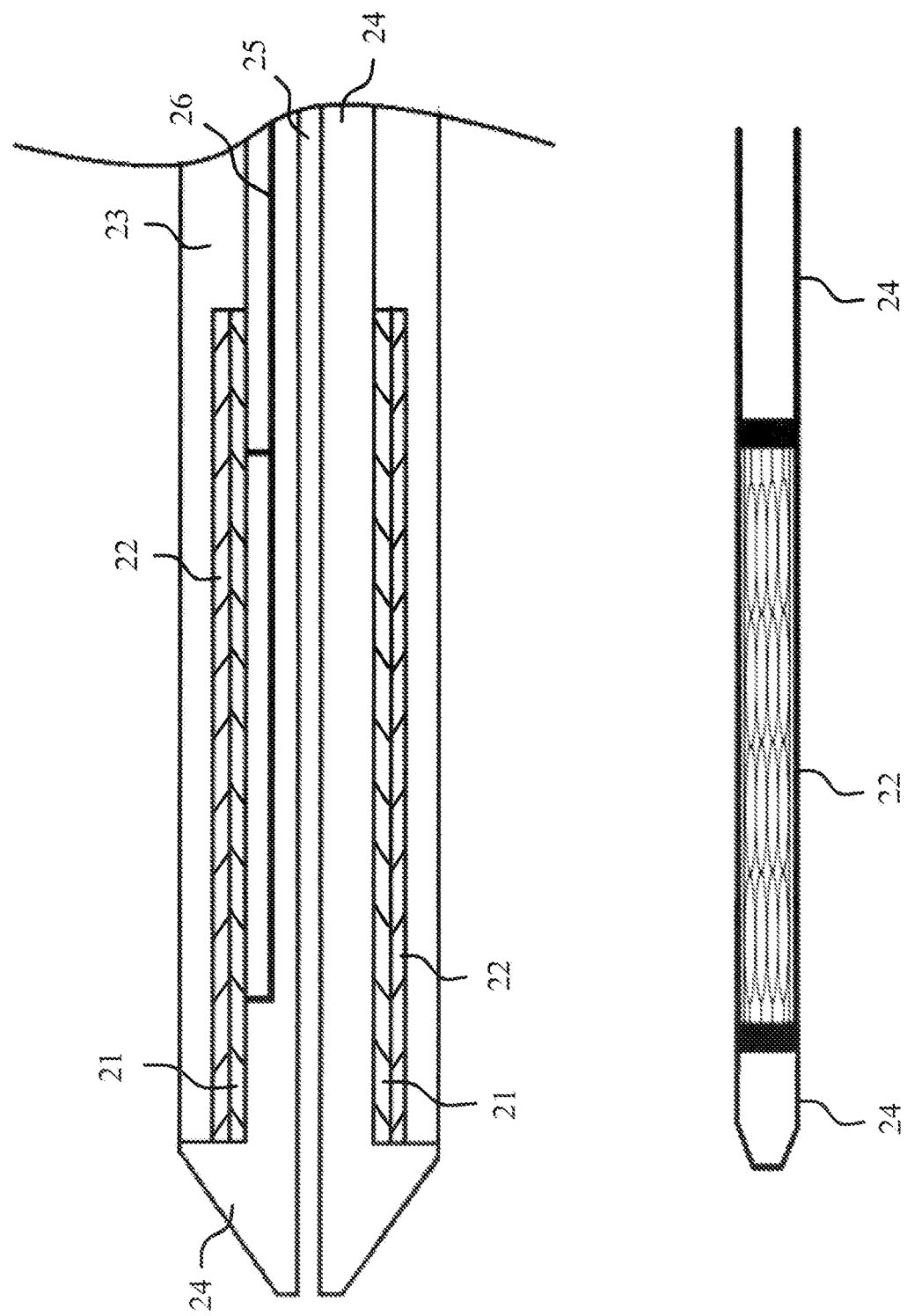
FIG. 2 illustrates the inner structure of the device in a cross-sectional fashion in an example of the invention.

The applied device according to the present invention is discussed in more detail in FIG. 2, showing a cross-section of the structure of the device. The sheath comprises an inner part 24 and an outer part 23. In the middle horizontal axis of the sheath there is a central tunnel 25 which may accommodate the control cable 14. The friction between the inner surface of the central tunnel 25 and the outer surface of the control cable 14 is preferably made small by selecting appropriate material parameters (e.g. a polymer for the sheath, a suitable metal for the control cable), or by adding lubricative liquid material between the control cable 14 and the inner surface of the central tunnel 25. Furthermore, it is possible to use a coated metal wire as a control cable 14 which makes the friction small with the adjacent surface material of its tubular path. Because the vein can be very curvy, the control cable 14 needs to be stiff enough in order to straighten the curvy vein when inserting the control cable 14 through it. A substantially straight vein is required for the longitudinal stent structure to pass smoothly along the vein to the desired location to be treated.

The lower part of FIG. 2 illustrates an exemplary design of a two-sidedly adhesive surface 22 which is compressed between the outer part 23 of the sheath and the inner part 24 of the sheath. The inner part 24 of the sheath is shown in this cross-sectional illustration and a longitudinal section is visible for the adhesive surface. The adhesive surface 22, which is shaped as a substantially tubular material, may have a closed-loop type of mesh structure which allows the compression and decompression of the adhesive material regarding its diametrical dimension. The adhesive two-sided surface 22 will have a longitudinal length with which the closure treatment is required length-wise within the human vein. The lower part of FIG. 2 just exemplifies this situation, and the adhesive surface section may locate in some other horizontal place with respect to the blunt end of sheath (shown in the left).

The balong 21 is a space which is fillable by a liquid, such as water. The balong 21 represents also a volume which is extendable with respect to the increasing volume of liquid. The volume of the balong is thus dynamic. By referring also to FIG. 1, the reservoir and fluid path 13 represents the incoming route, i.e. a passageway 26 for the fluid within the inner part of the sheath 11, 24. The passageway 26 for the inserted fluid may have one or several input branches into the balong 21 itself, exemplified in the upper part of FIG. 2 by two incoming fluid passageway branches, i.e. two short vertical sections from the horizontal passageway into the balong 21.

Now going to an exemplary structure of the sheath, the inner sheath can be divisible into two parts, e.g. into two halves, so that the inner sheath can be easily removed from the control cable after the inner sheath has been removed from the vein of the patient by a pulling movement. Regarding the outer part of the sheath, it can be an integrally tubular structure which can be pulled along its axis where the control cable also locates (i.e. in the central tunnel of the inner sheath). In an advantageous solution, the outer sheath is not splittable because after the pulling movement, the outer sheath movement will reveal the adhering surface of the tubular structure for a desired length while the other end of the outer surface will locate outside the patient's body around the control cable. Still, in other embodiment, the outer sheath could be also split in half along its longitudinal direction. Going back to the inner sheath with a split structure embodiment, the halved parts may in practice be connected together by a simple mechanical stub and hole-structure in the outer longitudinal end of the device which locates outside the patient's body in its normal using situation. The mechanical connection can be manually opened which releases the inner sheath into two half-circular parts when their cross-sections are concerned. With the end section opened in the device, the relevant parts of the inner sheath can be pulled out along the control cable outside the vein opening in the skin and removed as two halves of the cylindrical inner sheath from the control cable.

Still, in another embodiment, the present invention works well also when both the inner and outer sheaths are integral, non-splittable tubular pieces of elements, which slide along the control cable into the vein, inside the vein, and outwards from the vein. Furthermore, a beneficial structure according to the invention comprises a holding means to hold the inner sheath steady while the outer sheath is pulled out from the vein to a certain length. Such means can be an orthogonal directed short stub shown as elements 15a-15b in FIG. 1.

The mutually slidable principle of the inner and outer sheaths in view of one another in given longitudinal "steps" allows to reveal the adherable outside surface of the tubular material for a predetermined length at a time whereafter the balong can be filled for that specific length. The step length can be around 5 cm but other lengths can be selected as well. The balong can be filled for the determined length, revealing protrusions for that longitudinal length as well which will adhere onto the intima for that longitudinal length as well. The manual pressing (discussed in detail later) and the ultrasound inspection (also discussed later) can also be performed for the recently adhered step length only, already when the rest of the vein is still comprising the parts of the invented device. The manual pressing will take place when the liquid of the balong has been sucked out from the vein, and the inner sheath has been pulled out, as well as the control cable, leaving the tubular material with protrusions only present in the vein for the given longitudinal area. Such step-by-step procedure of filling the balong for just a shorter sub-length of the whole vein has an advantage where less liquid is needed for a single balong filling.

Back to the method according to the invention, when the device has been placed in the correct position within the vein, the sheaths can thus be pulled out or split into two halves and removed from the vein while pulling the sheath out. The outer part 23 of the sheath can be removed first. After that the adhesive surface 22 is either free to expand in a self-forcing (i.e. spontaneous) fashion, or free to expand under an external force exemplified by the use of the balong 21 fillable with a liquid. The balong 21 can be formed as cylindrically shaped volume with a ring-shaped cross-section where the central cylindrical part within the balong is not part of the balong volume because it houses the inner sheath and the central tunnel for the control cable. In the latter case, a medical professional can manually pump the liquid from the reservoir and along the passageway 26 so that the volume of the balong 21 fills up. The balong 21 volume is filled until the tubular adhesive structure 22 touches to the inner surface of the vein and applies a predetermined force towards the adhesive surface 22. The threshold force determined by the final liquid volume within the balong 21 is specified to be a force where the protrusions penetrate through the inner surface of the vein (i.e. the intima) along the whole desired longitudinal tubular area (i.e. cylindrical outer surface) of the adhesive surface 22. This threshold force can be specified to be a predetermined pressure value in the pump system of the balong. In other words, a proper force applied towards the intima of the vein is configured to be verified by a pressure measurement of the liquid insertion means of the balong 21. Another way is to verify the connection of the protrusions through the intima visually by ultrasound measurement with a respective transceiver device. The latter way is also applicable when the material is self-expansive, elastic material, where no balong is needed for forcing the protrusions of the tubular structure through the intima of the vein. In this way, the diameter of the de-compressed tubular adhesive structure (i.e. diameter of the extended protruded cylinder) is preferably slightly larger than the largest diameter in the blunt end of the inner part 24 of the sheath.

The balong 21 also can be used to detach initially stuck inner surface protrusions from one another when the balong 21 is filled. The structure can be internally stuck from their inner surface protrusions after the manufacture and during the transport of the structure, and the material expansion will not happen properly if the inner protrusions are stuck, unless a further force applying element, e.g. a balong 21, is provided. Because the shape of the protrusions allow detachment under force (e.g. for the barbs or curved hooks), they detach when the balong 21 is filled with a liquid, and at the same process, the outer protrusions will stick to the inner wall of the vein, as explained above. The balong 21 thus has an additional advantage of removing a defect (=mutually stuck inner protrusions before the actual expansion of the tubular adhering material) occurring because of the transport of the product from the factory to the operation room.

The tubular material, which comprises supporting material in addition to the protrusions, is preferable made of elastic material or having at least elastic properties. The elastic tubular material may be formed from compressable and decompressable mesh-type of structure, i.e. with certain shapes of holes, which allows the material to compress and de-compress considering its cross-sectional diameter. On the other hand, the tubular material can be intact and integral (i.e. with no holes in its outer surface) but made of elastic material such as rubber or elastomer, or of a mixture of at least two elastic materials. Preferably the material with elastic properties acts so that it does not comprise intrinsic forces after the expansion which would compress the expanded tubular material back towards the original size only by themselves. This means that the compression needs to be achieved through manual pressing operation on top of the skin in the operated area. If there would be an intrinsic force trying to compress the tubular material again after the expansion, there would be high risk that the attached protrusions would be released from the intima of the vein, thus making the closure process not an optimal one.

In this situation, the protrusions have hit the intima of the vein in the treated sub-length of the vein, and stuck there with a desired force or pressure acted e.g. through the filled balong and respective pressure measurement, for instance.

Next, the balong 21 can be emptied, i.e. the liquid can be pulled or sucked out from the balong. A respective pump and valve used to fill the balong can be also used to empty the balong. The liquid may be directed back to the reservoir through the path 13.

Because the outer protrusions have stuck into the intima of the vein, they will remain stuck even during and after the emptying of the balong 21.

After this step, the inner part 24 of the sheath can be removed from the vein with a pulling movement, together with the emptied balong 21 because the inner sheath and the balong with the liquid passageways locate as a mutually integrated structure in a preferred embodiment. The protrusions in the inner tubular surface of the tubular adhesive material do not stick with the inner part 24 of the sheath, because the "curved barb" structure will nicely slide away from the removed plastic surface of the inner part of the sheath. The same also applies for the outer part 23 of the sheath earlier, allowing easy removal of the sheath parts from the vein, thus exposing the curved barbs or generally, protrusions to expose for the latter connection purpose.

In case the balong is a separate element distinct from the inner sheath, the emptied balong can be removed first and the inner part of the sheath 24 can be removed after that by a manual pulling movement along the control cable out from the patient's vein.

After the inner part 24 of the sheath, the control cable 14 can be removed from the vein by a manual pulling movement.

All the steps of pulling out of a given part of the device can be performed by a given longitudinal distance at a time, after which the manual pressing step can be applied to the vein area comprising only the 2-sidedly adhesive tubular material within that given longitudinal area. Thus, the removal of the device parts and the end treatment on top of the patient's skin can be performed area-by-area along the patient's leg while a part of the inserted device still remains within the patient. The inspection of the vein closure quality can be inspected also step-by-step after each pressing step with an ultrasound transceiver device. It is even possible to perform the actual pressing with the ultrasound transceiver device on top of the handled skin area, thus combining the manual pressing and verification tasks to be performed with a single manual pressing movement. Only after the last longitudinal moving step of the invented parts of the device, the whole sheath and the control cable is fully removed from the vein, and the last manual pressing step will complete vein closure operation. A final check may still be applied for the whole treated vein area through external ultrasound inspection.

In other words regarding the use of the ultrasound verification, the end result of the process of closing the vein is configured to be verified by an ultrasound measurement performed for each treated sub-length of the vein after or during that particular sub-length has been or is manually pressed.

For the ultrasound transceiver device to work properly, there needs to be something in the vein area which reflects the ultrasound signal in an embodiment of the invention. In practice, in the outer blunt end area of the outer or inner part of the sheath may comprise a part made of metal. In an example, this may be a metal ring which is 5 mm wide. Such a reflective part (e.g. a metal ring) can be covered by a coating. Either the whole blunt end or a part of it may be made of such reflective material. In another option, the ring or other shape of the ultrasound reflective part can be made of another, non-metallic type of material, which reflects well the applied ultrasound signal in the treated vein area. When the ultrasound measurement is applied, all metallic parts of the device will reflect the ultrasound signal, such as the metallic parts of the tubular adhesive material as well as the end part of the sheath according to the above and the control cable, thus giving practical information to the medical professional about the locations of the protrusions and the device end (i.e. the sheath end) location within the vein during the performed vein closure operation.

An important practical feature during the vein closure operation is to keep a part of the outer sheath always inside the vein, near its entrance hole (i.e. the surgical cut), e.g. for a length of 3-10 cm in order to use it as a barrier for outflowing blood. In other words, the treatment of the vein is configured to be performed in a step-wise manner for a given longitudinal length at a time while a part of the outer part 12, 23 of the sheath remains in the surgical cut of the vein to prevent blood loss during the treatment.

When all the device components have been removed from the treated area (defined also by the given longitudinal distance defined in previous paragraph), except the two-sidedly adhesive tubular material 22, which is now stuck into the inner walls of the vein with the protrusions in the outer surface of the tubular adhesive material, the process may enter its final manual step. Then, the protrusions in the inner surface of the tubular material are also free of any external material, thus allowing the final step of the vein closure method.

In the final step, the skin area on top of the treated vein can be pressed manually, e.g. by hand of the medical professional. The skin area to be pressed needs to locate on top of the area where the protruded adhesive material now locates. The pressing external force now forces the cross-section of the vein to flatten and during the flattening of the vein in this area, the inner protrusions of the two-sidedly adhesive material will stick into one another. Of course some of the inner protrusions may have stuck already within one another but the manual pressing force will make sure, this self-sticking will happen along the whole protruded area of the adhesive material within the treated vein area. As the shape of the protrusions makes sure that the outer protrusions will keep stuck within the tissue of the inner surface of the vein, the substantially same protrusions in the inner side of the tubular surface make sure that the protrusions stick to one another. After the whole needed skin area has been manually pressed, the end result is an efficiently closed cross-section of the vein in a given longitudinal length. This in medical terms means that this particular vein is dead, and thus, unable to pass any blood through it. This is an efficient way of treating CVI and other venous malfunctions by closing the vein.

Of course, it must be noted that any vein section still comprising the control cable and possible other physical parts of the device (like the sheath) must not be pressed manually. The medical professional needs to be accurate in locating the correct pressing area in view of the remaining device parts still present within the patient's vein.

In other words, through manual pressing force applied to the skin of the patient along the area of the treated vein, the outer adhesive surface of the tubular material 22 is capable to attach to the inner surface of the vein, and the inner adhesive surface of the tubular material 22 is capable to attach with its own counter-surface, thus closing the vein. Because the tubular adhesive material 22 is flexible, the inner surface will adhere to its respective counter-surface with similar protrusions, and the end result is a flattened two-layer thick structure stuck on top of one another and also to the vein walls obtained with two-sided protrusions of both "layers".

Because an external material has been inserted into a human body, the tubular adhesive material must not have any undesired consequences within the human body even in the longer term. This is achieved by selecting the adhesive material to be a soluble material within a human body, at least partly. The soluble materials are as such known in the art, such as processed collagen or monocryl. However, in one embodiment of the invention, the soluble protrusions in the tubular structure can be completed with a certain non-soluble set of protrusions. In practice, the tubular adhesive surface may have given locations in its longitudinal axis along which a single or plurality of rings of metallic protrusions are placed. These metal rings of protrusions can be used so that there are a few (e.g. 2-4) rings of metallic protrusions along the whole adhesive tubular surface. After a longer period of time after the vein closure operation, the soluble protrusions have been solved by the human white blood cells (i.e. leukocytes) through a minor flammation reaction so that there is no visible trace of the solved protrusions in the tissue anymore. Still, the metal protrusions keep stuck in given longitudinal locations within the vein internal surface, making sure that the closing material is kept fixed in its place in the vein. Small amounts of metal within these few rings of protrusions is not that harmful to the patient, and usually there are no health related effects with such a minor amount of metal within the vein walls. The protrusions are very short, which means that their effect is minor regarding any inflammation processes within the tissue. The result is a scar in the tissue, but usually the patient does not even notice that small metal residues will stay in these few locations along the vein. This is a notable advantage of the presented embodiment of the invention. Even in the embodiment of using a totally dissolving set of protrusions along the whole tubular material, the device indeed leaves no hazardous material within the human body after the solving process has been completed. This is a clear advantage of using soluble protrusions in the inserted device.

In an embodiment, the selection of a soluble (i.e. dissolving) material in the present invention depends on the desired tensile strength of dissolving adherable material. For instance, there can be a requirement that the tensile strength of the adherable material remains at least 50% of the initial tensile strength for a 3 months period, in order for the vein to close finally in a reliable manner. If this requirement is fulfilled for a candidate material, it can be selected as the dissolving material. The requirement can be a minimum time which a certain tensile strength is guaranteed to be present for the given soluble material. In the other hand, the requirement can be a required tensile strength after a given period of time. This depends on the treated vein type and also on the vein diameter. The minimum time can be called as a resorbing time for the selected material. These different characteristics of the vein may require different resorbing time requirements for the dissolvable material. In one embodiment, the resorbing time can be selected from a range of 3 weeks to 1 year, and the dissolving material is selected based on this parameter. The end effect in this regard is that the selected resorbing time of the dissolving material must be long enough to ensure that no vein recanalization will take place. This means the same as a consistently closed vein even after a longer time period.

In another embodiment discussing the fixation of the tubular material with non-soluble protrusions, the metallic protrusions may locate in two or four longitudinal direct lines along the longitudinal direction of the tubular material. This means a 90 degrees difference of the fixed metallic adhering lines in view of the rings of the previous paragraph (i.e. in view of the planes of the rings). The two or four longitudinal metallic protrusion lines may preferable locate symmetrically opposite one another to obtain a symmetric fixing along the intima of the vein. Also in this embodiment, the rest of the protrusions are preferably made from soluble material with a desired density along the tubular material surface in both sides.

A further advantage of using the fixed structure with metallic ring or rings of protrusions, or metallic longitudinal connection lines of protrusions, is that this decreases a risk for obtaining pulmonary embolism. When all parts are strongly fixed within the vein, the risk for any travelling blood clot into the lungs also decreases. Pulmonary embolism is a severe health issue and thus, the probability for such effects has to be as minimized as possible.

A further advantage is that when the balong is used in the structure of the device, there is no need for having protective plastic film on the inner surface of the adhesive tubular surface. When the balong is filled with the liquid, the possibly self-adhered protrusions in the inner tubular surface will detach and the structure will expand towards the vein wall, adhering the tubular material to the wall with the outer protrusions. An advantageous characteristic is also that the end result comprising the two-sidedly adhered tubular material as a closing means for the vein, does not maintain any internal forces which would rip apart the closure. The inner surface will remain stuck with its own internal counterpart surface, and simultaneously the outer protrusions will remain fixed through the intima without any restoring, internal forces present. This ensures that the end result of the vein closure area is stabilized and safe for the surrounding healthy tissues around the vein.

It is notable that while the above paragraphs disclose tubular adhesive material, this material is reshapeable regarding its cross-sectional form, which is illustrated by the fact in the method steps, where the expanded material will finally be collapsed, i.e. flattened manually by an external pressing force. In the final, treated situation of the patient, the tubular material is reshaped as a mutually stuck, double-layered structure within the treated vein.

Discussing other advantages resulting in the use of the device according to the invention, there is no need for excessive pricking of the treated tissue of the patient. Usually a single anaesthetic pricking action is required when the operation is started. This makes it a quicker procedure, cheaper, and convenient for the patient during the operation. Also no support stocking is required after the operation, making it more convenient for the patient also for the aftermath of the operation. Furthermore, there is no need for expensive laser of RF energy sources in the title application. As a result of this, the invented method and device does not result into generated heat, possible burns, or chemical irritation. The method also enables the device to be used along the whole vein length from the ankle towards near the groin area in the lower leg or thigh. Because a majority or even all of the protrusions are made of soluble material, the end result after a given time period is a very small amount of external material within the human body. This happens because the leukocytes in the human blood will "melt" the soluble material away through a minor inflammation reaction, which will fade away and heal in a rather short time. This is a long-term advantage of the method and device according to the invention. A further advantage of the used device is that it is in practice size-independent regarding the vein diameter. The only condition is that the sheath diameter must be small enough for the sheath to enter and pass along the vein. Otherwise, the treated vein area may have a rather large range of diameter, where the device will work because of the self-expansioning characteristic or because the use of the balong. A single type of device with given dimensions is thus applicable for various different diameters of applied veins. Therefore, it can be also noted that the invented device is applicable and works well for veins having a diameter over 6 mm as well, where the foam is not applicable (see the prior art).

A further advantage of the invention, which is also significant for the patient, is that the risk for generating a nerve injury (e.g. for the small saphenous vein in the lower leg) is substantially lower than with many prior art methods. Thus, the undesirable result of generating a loss of sense onto the heel of the patient is very improbable, and in practice negligible.

The result of the performed vein treatment can be verified through an ultrasound measurement, as mentioned earlier. It will reveal whether the closure is good enough for a single used device after the operation. If necessary, a further device according to the invention may be additionally inserted. In case some of the two-sidedly adhesive material is unattached to the vein wall, and/or to itself, repeating the manual pressing action in the relevant skin area may correct this defect as such. The ultrasound verification of the closure quality can be made step-by-step after a partial removal of the sheaths and the control cable and each manual pressing step, so that the vein treatment is performed area-by-area longitudinally along the vein. Additionally, a complete final verification may be performed separately for the whole completed, treated vein length with the ultrasound measurement device. The ultrasound measurement device as such can be selected from the ones used in current medical practices, i.e. from devices known in prior art.

Figure 3:
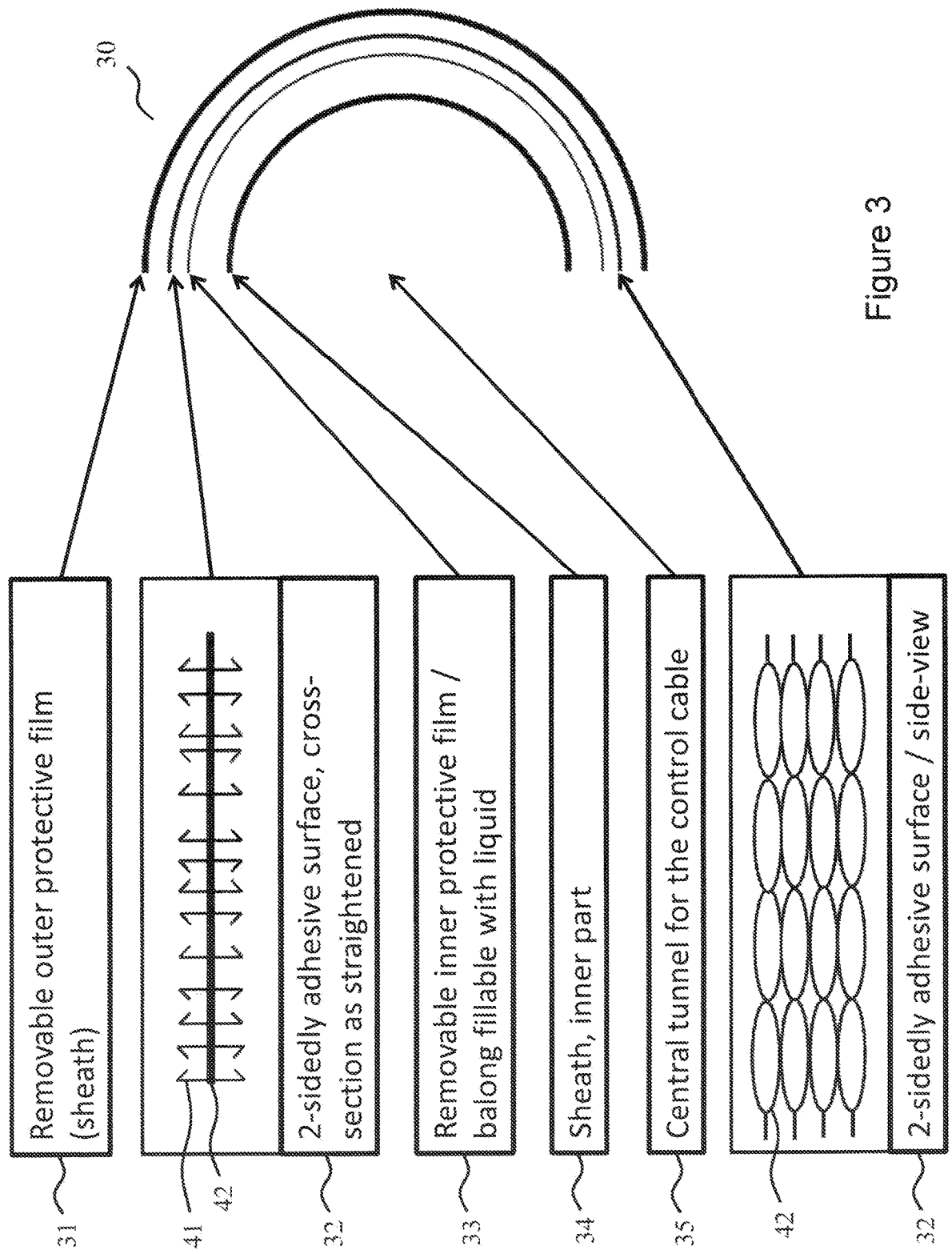
FIG. 3 illustrates an example of the layers and their mutual order in the tubularly formed device in a schematic fashion.

Going back to an advantageous example of the device according to the invention, the structure in FIG. 3 is now referred. The structure conforms with the embodiments presented in view of FIGS. 1 and 2.

In other words, FIG. 3 illustrates an embodiment of the layer structure 30 of the device. The layer structure 30 is shown as a cross-section of a tubularly shaped device where a halved section is shown in the right. Some layers are shown as straightened sections for merely simplified and illustrative purposes.

The outermost layer in this embodiment is a removable outer sheath or a removable outer protective film 31, whose purpose is to cover and protect the protrusional next surface from sticking onto the vein walls before it is pushed into its correct place within the treated vein area. The outermost layer 31 may be manufactured from hard plastic material, or it can be a polymer-based thin plastic film. A requirement for a thin film is that the protrusions under it should not break the thin film when the device is moved along the vein, and of course also during the transport of the device from the manufacturing facility to the operating room of the patient.

In other words, regarding the possible outer protective film 31, the outer part 12, 23 of the sheath is a protective film with hydrofilic properties, which protective film is manually removable from the vein or towards outside of the vein through a pulling movement. This ensures a step-by-step treatment for given sub-lengths of the vein in a subsequent manner, from the most remote section of the vein towards the surgical cut (i.e. where the instruments are inserted into the body). This is discussed elsewhere in detail. Instead of an outer protective film made of e.g. a thin plastic film, an outer part of the sheath with slidable properties can be used, which outer sheath can be manufactured from harder materials, such as hard plastic. The slidable properties are discussed elsewhere in detail, for both the inner and outer parts of the sheath.

The next layer is the two-sidedly adhesive tubular material 32, which has protrusions 41 in both sides of the tubular structure along a desired longitudinal length of the device where the attachment is desired. In this illustration, the protrusions 41 have a shape of sharp hooks but this is merely a single example of all possible shapes within the inventive concept. The shape of the protrusions 41 can be a barb, generally a hook, a curved end resulting in a blunt end or a sharp end, and also a protrusional end with a 90 degrees turning short section is possible. The end of the curved or hooked end of a protrusion 41 may have a thicker, ball- or drop-shaped end in order to enhance the grabbing characteristics into the vein walls. The end section may be a sharply turned but a direct piece of a barb. Furthermore, a protrusion 41 may be a rounded piece of barb along the whole short length of the barb. In an embodiment, the barbs may be formed in sub-branches where a single outward protrusion may divide into e.g. three sub-branched protrusions. Thus, a single main protrusion may have several hooked ends enhancing the grabbing properties of the tubular adhesive material. The end of each protrusion 41 may be shaped like an arrow in a further example of the invention. It is also possible that the group of protrusions 41 have two or more different shapes. It is possible to use a first shape for the metallic rings of protrusions in given longitudinal places of the device, and a second shape for the rest of the protrusions made from the soluble material vanishing over time in the human body. As a summary, many different shapes perform well in the context of the present invention. The possible shapes partly imitate Velcro strap structures but the present invention is broader, comprising any curved or angled, barb- or hook-shaped form for the protrusions 41. Also the dimensional length of each protrusion 41 must be small in order to attach well but without harm to the inner walls of the treated vein.

In other words regarding possible shapes of the protrusions 41, the protrusions 41 can be shaped as thorns, spines, prickles, arrows, or as blunt or sharply shaped barbs, or as curved hooks, either with or without a drop-shaped thicker end part.

The supporting material 42 of the adhesive layer shown in FIG. 3 as the horizontal part where the protrusions 41 are all attached to, can be preferably made from soluble material which is bendable to form a tubular main structure for the adhesive layer.

The lowermost box in FIG. 3 refers also to the two-sidedly adhesive surface 32 but it emphasizes the compressable mesh-type of structure for the supporting material 42 of the adhesive layer 32. In this exemplary illustration, the supporting material 42 (protrusions not shown here) may have closed adjacent loops along the whole tubular structure. A single loop may have an elliptical shape and each loop may have four connection points to adjacent loops, as shown. The ellipse can have a clearly longitudinal shape. However, any other form or shape or structure of a mesh-type supporting material is possible. Also the same effect can be obtained by selecting a non-hollow, elastic material such as rubber, elastomer, or even a woven flexible fabric made of a suitable material. The main characteristic of the supporting material is that during the manufacture of the device, the supporting material can be compressed between the outer sheath 31 and the inner sheath 34. When the outer sheath 31 has been removed, the supporting material may then de-compress so that its diameter increases. In other words, the supporting material being capable to physically compress and expand (i.e. decompress) in the radial direction is the main characteristic in this regard, and not the physical structure or the material selection as such. The automatic de-compression or self-expansion is required in the case where no balong is used but only an inner protective film is used as layer 33. With the use of the balong, the mesh structure may still be used so that under the force of the balong filled with liquid, the mesh structure of the supporting material 42 will expand, i.e. de-compress because of the applied force. Elasticity of the supporting material 42 is thus a necessity.

A mesh-type supporting material may comprise both dissolving and non-dissolving material parts. Also the elastic (i.e. non-mesh-formed) supporting material can be at least partly manufactured from dissolving material, and the rest can be made from non-dissolving material.

The dissolving material can be processed collagen or monocryl, for instance. The non-dissolving material can be made of a metal or as a mixture of several metals.

As the next layer 33 towards the center of the layer structure 30, there is either a balong fillable with liquid or a removable inner protective film. While the use of the balong has definitive advantages (see above), it may still be replaced by a plastic protective film, which can be manually pulled out from the inner surface of the adhesive tubular layer. The inner plastic protective film works well in the situation where the adhesive material 32 is a compressed structure diameter-wise, enabling self-expanding properties when its outer protective film or sheath 31 is removed.

As the innermost layer shown here for the layer structure 30, there is an inner part of the sheath 34. This tubularly shaped structure can be manufactured from hard plastics, and from similar material as the outer part of the sheath 31. The sheaths (both parts 31, 34) can be split structures (not shown) where the sheath can be removed from the control cable as split halves immediately after the sheath has been pulled out from the vein (in case a longer control cable is used). Still, a split structure is not a necessity, and the same effect can be obtained by just pulling (i.e. sliding) the outer or inner sheath along the control cable out from the patient's vein.

The inner part of the sheath 34 comprises a longitudinal central tunnel 35 which is meant for the control cable (the control cable itself is not shown in FIG. 3). Hydrofilic properties are desired in a preferable embodiment in the inner and outer surfaces of the sheath so that the sheath moves smoothly along the control cable, and on the other hand, in view of the vein's inner walls. The width and material of the control cable can be selected in certain range, but preferably it is thick enough enabling the straigthening action on curvy veins when the control cable is inserted and passed into and along the vein. A preferable material for the control cable is metal, such as steel or aluminum, because the control cable is designed to only temporarily be accommodated in the human vein. Of course the material must not be chemically irritative for the human body. The smoothness of its surface is also a practical necessity. The end of the control cable can be designed to be blunt so that it does not break through any part of the inner walls of the vein when passed along the vein. Still, in an embodiment, a section in an insertable end of the control cable into the human vein can be curvable and thinner cable in view of the rest of the control cable, allowing smooth progress of the control cable with a manual rotating movement.

Figure 4:
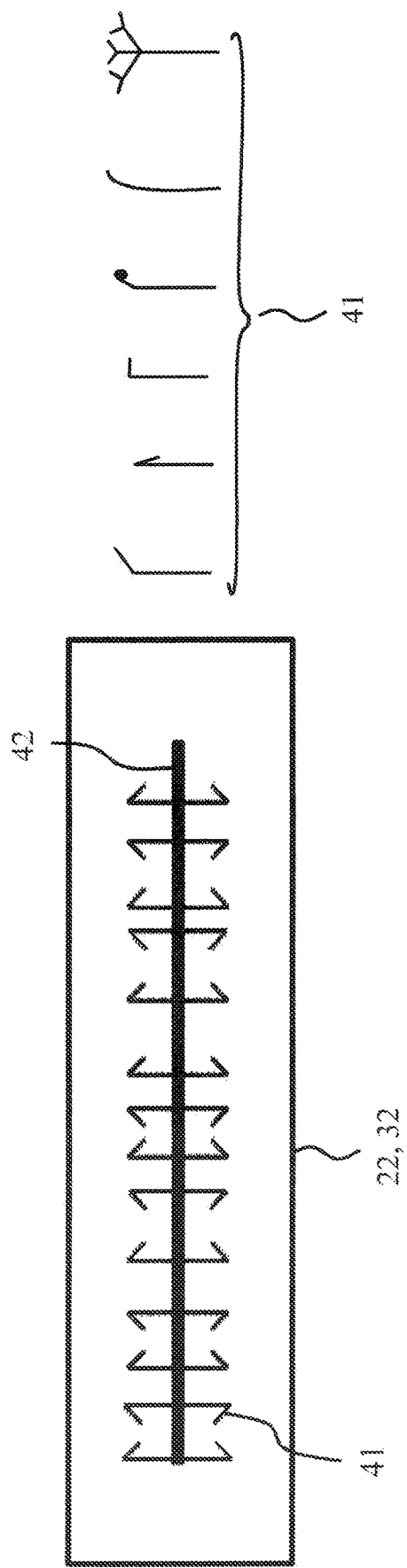
FIG. 4 illustrates examples of the shapes of the protrusions used in two-sidedly adhesive tubular material.

FIG. 4 illustrates the two-sidedly adhesive material 22, 32 in a straightened form once more. The material comprises the supporting material 42 and the plurality of protrusions 41. The protrusions 41 can be uniformly distributed along both the inner and the outer surfaces of the adhesive material. This means that they may have uniform i.e. constant gaps between one another along the whole adhesive surface. In the left hand illustration of FIG. 4, the protrusions 41 are depicted in the shape of sharply angled spike on top of an orthogonally protruding section from the supporting material 42. This is merely one possible shape for the protrusions, as discussed also earlier. The right hand side of the illustration shows six more examples of the possible shapes of the applied protrusions 41. The first of these is a bluntly angled spike on top of an orthogonally protruding section. The second one is a very sharp, i.e. an arrow-like shaped protrusion. The third one depicts an orthogonally deviating barb from the main barb branch. The fourth one is a bit like the first option in the right hand side of the illustration but its end is provided with an added thicker drop-resembling part. This kind of a shape offers a better attachment of the barb because after this protrusion has penetrated the inner wall of the vein, it can not be easily removed from the tissue. Such a drop-shaped end can be supplied in any of the other shaped protrusions as well to ensure better attachability. Going to the fifth example in the right hand side of FIG. 4, it shows a slightly curved protrusion. The curvature radius is shorter in the outer end of the protrusion 41 than near its fixing location to the supporting material 42. The sixth and final example of the possible protrusion shape is a multi-branch spike or protrusion, where the main protrusion can be in several sub-branches, here to three sub-branches. Furthermore, these three sub-branches have two outer extensions each, in order to create a bit tree- or plant-like structure where there are multiple penetrational points within a single main protrusion. This kind of a structure allows a more efficient type of attachment into the inner walls of the veins but of course, it is a bit more complex to manufacture.

The protrusions 41 may generally have also other shapes than the illustrated ones. The main characteristic or condition of the protrusions is that the protrusions have sticking i.e. penetrating capabilities slightly into the inner walls of the human veins, and that after the manual pressing action has been performed, the protrusions won't be released from the tissue in regular human movement activities nor when pressing later the relevant section on the skin. In other words, this generally means that the balong or self-expansive force is capable to press the protrusions into the tissue, but the protrusions won't be able to release after that from the tissue.

The connecting rings of protrusions made of metal can be selected to have any of the possible shapes, comprising the ones illustrated in FIG. 4. In yet another embodiment, a single ring of protrusions can be multiplied to strengthen the fixing points onto the vein; e.g. by having two adjacent rings of protrusions made of metal and having a selected form of protrusion. Also in this case, the intermediate protrusions are preferably then manufactured from a soluble material, the same applying also for the supporting material 42.

Figure 5:
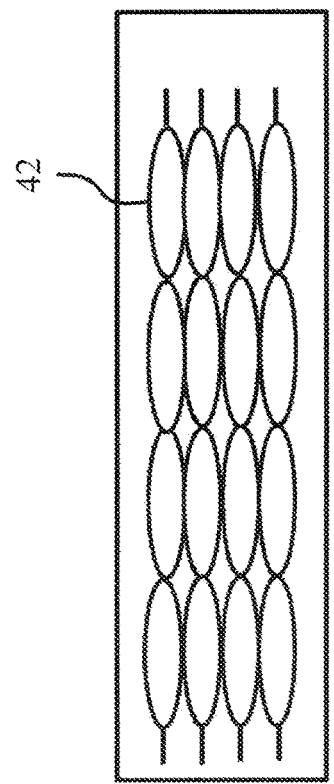
FIG. 5 illustrates a possible design used in the mesh-like supporting material of the adhesive tubular material capable of compressing and de-compressing.

FIG. 5 illustrates a possible shape of a mesh-type of network applicable for the supporting material 42 capable to change its diameter of the tubular form. The illustration describes the above discussed oval-based network shape, which has good compressing and de-compressing properties. The illustration is a schematic image of a possible structure. Still, other shapes in the holes are usable as well in order to obtain the desired effect. However, a compressable and de-compressable (i.e. expandable) material is the main operational characteristic here, and the material can also be made from elastic, non-hollow tubularly shaped material surface (the non-hollowness meaning the curved cylindrical surfaces).

Regarding certain dimensions in the invented device, the length L of the protrusions 41 can be selected between the range of 0.5 mm L 1.0 mm, thus allowing the protrusions to penetrate the intima of the vein into the muscle layer. Regarding the filled balong diameter d, it can be in the range of 5 mm d 30 mm, depending in the treated vein diameter in the operated area of the vein. The treated vein type also affects this. The advantage of the invention is that a wide range of veins regarding their diameter is well treatable with the invented type of device. A single device has thus good applicability in different sizes of veins.

In an example of the device, the outer surface of the inner part of the sheath (see FIG. 1) may comprise a measurement scale e.g. between 1 cm:s or between 5 cm:s. The scale can start from holding means 15b and increase to the left. The purpose of this feature is to illustrate the user, i.e. the medical professional, the desired sub-length within the vein, which measure corresponds to the length of the "opened protrusions", or the length of the balong in a single step of the treatment. If the holding means 15b is slided by 5 cm from element 15a, thus the inner sheath 11 sliding 5 cm in view to the outer sheath 12, the device will reveal 5 cm length of tubular protrusions within the adhesive tubular structure. The medical professional can now more easily select the operating sub-length in a single step of the vein closure process. This is also useful for determining a correct amount of liquid filled into the balong in a single process step. Of course, the pressure measurement of the liquid can assist in obtaining the right force for the protrusions to penetrate the intima of the vein into the muscle layer, thus resulting in proper fixation of the tubular adherable material onto the vein walls.

In yet another embodiment of the invention, the tubular material 22 can be formed with alternating sections along its longitudinal length. For instance, there can be adherable sections between non-adherable sections in alternating fashion. In practice, the supporting section provided with protrusions forming the 2-sidedly adherable section can be followed by only the supporting section without any protrusions. This way there is less need for the 2-sidedly protrusional material but the closure will still take place. It is possible to manufacture the mere supporting section part from both soluble (i.e. dissolving) and non-soluble (i.e. non-dissolving) materials, like the adherable tubular material as disclosed earlier. This means that a part of such a supporting section will remain in the vein even after a longer period from the operation. The purpose of such a physical barrier within the vein is to create "a sealing plug" for possible metallic protrusions which might otherwise migrate along the vein. In the worst case, such a metallic protrusion or several protrusions may propagate along the vein to a dangerous location within the patient's body. It is important to ensure that no physical parts will propagate i.e. migrate along the blood circulation paths within the patient's body because they may cause serious harm elsewhere. Regarding the first sub-length with a protruded supporting section, its starting end can be provided with a couple of metallic protrusion rings, ensuring that the start of the adhering tubular material will tightly attach to the intima of the vein, and remain so during longer periods of time. This kind of end in the tubular material will act as a sealing plug for the small metallic parts elsewhere in the tubular material which metallic parts could detach during times and pose a danger for the treated patient.

As a further embodiment, the two-sidedly adhesive tubular material 22 can be manufactured from two adjacent and opposite layers with protrusions 41 which layers are sewn or otherwise connected together. This is an easier manufacturing method for the 2-sidedly adherable material. In another embodiment, the two-sidedly adhesive tubular material 22 can be manufactured from a single woven layer where the protrusions are added to both surfaces of a planar and rectangular woven layer. The planar piece of the woven layer of a desired size can then be woven together from opposite ends of the rectangular piece to form the two-sidedly adhesive tubular material 22.

As a yet further embodiment, the protrusions 41 can be aligned in at least two different directions when inspecting an opened, planar adherable material within its single surface. This means that the barbs or hooks can be sharp spikes, or desiredly cut elements, or cut edges, which can be aligned in at least two different directions.

The projections of the barb directions (i.e. their curved ends) onto the supporting material 42 may be directed to opposite i.e. 180° directions. The protrusions may even be placed in an alternating manner along the whole adherable surface, in their lines and columns. When the balong has been filled, the device within the vein can be pushed and pulled just slightly, and also rotated left and right also slightly. These small movements ensure that the protrusions 41 will penetrate through the intima into the muscle area of the tissue. Because the barbs are pointed to different or even opposite directions, this means that after the material has penetrated the intima of the vein, it will stay there as fixed arrangement, no matter how the material is pushed, pulled or rotated after the penetration. Such a protrusional structure will ensure a very good attachment of the tubular material through the intima of the vein, and it ensures a good-quality closure for the treated vein, i.e. a satisfactory end result for the operation.

The device, i.e. the material, according to the present invention is applicable to any symptoms or diagnosed disease involving vein insufficiencies or other medical conditions requiring closure of at least one vein. While in the above a device is referred in many sections, the invented material is basically a layered structure having unintroduced properties initiated by layer removals made manually. Thus, the device does not require any electricity to work, but it is a manually handled tubular structure with active adhering properties when it is in a correct place in the vein. The validation of the treatment result can be performed with an ultrasound transceiver, but this is not part of the invented material (i.e. device) as such.

The inventive concept also comprises the method of inserting the material into the vein, removing parts of it from the vein in a given order thus exposing the adhering surfaces, and the manual pressing of the skin area performed by a medical professional to finish the adherence result for closing the treated vein.

The present invention is not merely restricted into the embodiments presented above but the present invention may vary within the scope of the claims.

The invention claimed is:

1. A tubular device configured to close an insufficient varicose vein of a human patient, comprising:
   a removable control cable, a sheath, and a two-sidedly adhesive tubular material;
   the removable control cable being made of metal, and configured to be inserted into the vein for guiding insertion of the sheath into the vein,
   the sheath having an inner and an outer part longitudinally slidable in relation to one another, the inner part of the sheath having a central tunnel configured to accommodate the removable control cable, and
   the two-sidedly adhesive tubular material having a longitudinal length equivalent to a length of the insufficient varicose vein to be closed and located between the inner and outer parts of the sheath, wherein
   the two-sidedly adhesive tubular material has a diameter that is expandable either in self-acting fashion or as a response to pressure originating from inserted liquid inside the two-sidedly adhesive tubular material and configured to attach to an intima of the vein upon removal of the outer part of the sheath from the vein,
   and the two-sidedly adhesive tubular material is further configured to have adhesive properties created by protrusions on an inner surface upon removal of the control cable and the inner part of the sheath from the vein, wherein the protrusions are configured upon external manual pressing force to the longitudinal length to attach to each other and stick into one another along the longitudinal length and result in a closed cross-section of the insufficient vein along the longitudinal length.

2. The device according to claim 1, wherein the outer part of the sheath is a protective film with hydrophilic properties, which protective film is manually removable from the vein through a pulling movement.

3. The device according to claim 1, wherein the protrusions are shaped as thorns, spines, prickles, arrows, or as blunt or sharply shaped barbs, or as curved hooks, either with or without a drop-shaped thicker end part.

4. The device according to claim 1, wherein the protrusions comprise a plurality of branches and sub-branches, where each end of the sub-branches are shaped as barbs or hooks.

5. The device according to claim 1, wherein the two-sidedly adhesive tubular material comprises a compressable network structure or otherwise elastic material configured to self-expand or to expand under applied force upon removal of the outer part of the sheath by pulling outwards from the device and the vein.

6. The device according to claim 1, wherein the device comprises a balloon inside the two-sidedly adhesive tubular material, which balloon is fillable at least partly with a liquid, creating a force expanding the two-sidedly adhesive tubular material in an outwards direction towards an inner surface of the vein.

7. The device according to claim 6, wherein the inner part and the outer part of the sheath are slidable longitudinally in relation to one another which movement releases the two-sidedly adhesive tubular material to expand either in self-expanding fashion, or through filling of the balloon with a liquid.

8. The device according to claim 6, wherein a proper force applied towards the intima of the vein is configured to be verified by a pressure measurement of a liquid insertion means of the balloon.

9. The device according to claim 1, wherein the device comprises an inner protective film without a balloon, configured to prevent the inner surface of the two-sidedly adhesive tubular material to stick to itself before expansion of the diameter of the two-sidedly adhesive tubular material in the vein has taken place.

10. The device according to claim 1, wherein the outer part of the sheath is configured to have a hydrophilic surface or coating allowing slidable motion of the sheath inside the vein.

11. The device according to claim 1, wherein the device comprises non-dissolving material protrusions in given longitudinal locations of the two-sidedly adhesive tubular material allowing an device to fix and maintain within the inner surface of the vein over time.

12. The device according to claim 11, wherein the device comprises dissolving material protrusions longitudinally between the non-dissolving material protrusions, which dissolving material protrusions will keep initially attached to the inner surface of the vein after removal of the device, and thereafter, the dissolving material protrusions are configured to dissolve by white blood cells of the human body over time.

13. The device according to claim 12, wherein the dissolving material protrusions are processed collagen or monocryl, and the non-dissolving material protrusions comprise metal.

14. The device according to claim 1, wherein the device comprises non-dissolving material protrusions symmetrically along at least two longitudinally directed lines along an outer surface of the two-sidedly adhesive tubular material, while the rest of the protrusions are made of dissolving material.

15. The device according to claim 1, wherein the two-sidedly adhesive tubular material comprises a supporting material, which supporting material is at least partly manufactured from dissolving material.

16. The device according to claim 1, wherein a length L of the protrusions is selected between the range of 0.5 mm≤L≤1.0 mm, thus allowing the protrusions to penetrate the intima of the vein into the muscle layer.

17. The device according to claim 1, wherein the device is configured to be removable partly from the vein after its insertion, where first the outer part of the sheath is configured to be manually pulled out partly from the vein, thereafter the two-sidedly adhesive tubular material is diametrically expanded either in self-acting fashion or through a manually fillable balloon, thereafter the inner part of the sheath without a balloon or with an emptied balloon is configured to be manually removable from a treated area of the vein, whereafter the control cable is configured to be manually pulled out from the treated area of the vein, resulting in only the two-sidedly adhesive tubular material comprising a supporting material and the protrusions to remain in the treated area of the vein before the manual pressing force is performed to the treated area of the vein.

18. The device according to claim 17, wherein treatment of the vein is configured to be performed in a step-wise manner for a given longitudinal length at a time while a part of the outer part of the sheath remains in a surgical cut of the vein to prevent blood loss during the treatment.

19. The device according to claim 18, wherein the end result of a process of closing the vein is configured to be verified by an ultrasound measurement performed for each treated sub-length of the vein after or during that particular sub-length has been or is manually pressed.

20. The device according to claim 1, wherein the device comprises alternating sections of the two-sidedly adhesive tubular material and mere supporting material, where the mere supporting material comprises non-dissolving material acting as a sealing plug for the protrusions.

21. The device according to claim 1, wherein the two-sidedly adhesive tubular material is manufactured from two adjacent and opposite layers with protrusions which layers are sewn or otherwise connected together.

22. The device according to claim 1, wherein the protrusions are aligned in at least two different directions when inspecting an opened, planar adherable material within its single surface.

* * * * *